United States Patent [19]

Gustilo et al.

[11] Patent Number: 5,800,437
[45] Date of Patent: Sep. 1, 1998

[54] CANNULATED TAMP AND CENTERING ROD FOR TOTAL JOINT ARTHROPLASTY

[75] Inventors: Ramon B. Gustilo, Eden Prairie; Todd J. Hein, Minneapolis, both of Minn.

[73] Assignee: Orthopaedic Innovations, Inc., Golden Valley, Minn.

[21] Appl. No.: 728,299

[22] Filed: Oct. 8, 1996

Related U.S. Application Data

[63] Continuation-in-part of Ser. No. 528,063, Sep. 14, 1995, Pat. No. 5,601,564, which is a continuation of Ser. No. 158,603, Nov. 24, 1993, abandoned.

[51] Int. Cl.$^6$ .................................................. A61F 5/00
[52] U.S. Cl. .................. 606/86; 606/79; 606/80; 606/84; 606/85; 606/87; 606/95; 606/96
[58] Field of Search ..................... 606/79, 80, 83, 606/84, 85, 86, 87, 88, 89, 92, 95, 96

[56] References Cited

U.S. PATENT DOCUMENTS

| | | |
|---|---|---|
| 5,089,004 | 2/1992 | Averill et al. |
| 5,108,405 | 4/1992 | Mikhail et al. |
| 5,147,408 | 9/1992 | Noble et al. |
| 5,180,388 | 1/1993 | DiCarlo |
| 5,192,283 | 3/1993 | Ling et al. |
| 5,197,967 | 3/1993 | Wilson |
| 5,222,955 | 6/1993 | Mikhail |
| 5,234,433 | 8/1993 | Bert et al. |
| 5,312,412 | 5/1994 | Whipple |
| 5,324,293 | 6/1994 | Rehmann |

Primary Examiner—Michael Powell Buiz
Assistant Examiner—Daphna Shai
Attorney, Agent, or Firm—Gregory F. Cotterell

[57] ABSTRACT

A method of preparing an intramedullary canal of a bone for joint arthroplasty including drilling a hole into the intramedullary cavity of a bone and inserting a centering rod longitudinally into the intramedullary canal of the bone. The rod is inserted to align the rod along the longitudinal axis of the bone. Osteotomizing the articulating surface of the bone and preparing the intramedullary canal of the bone to receive a prosthesis. The preparation including placing cannulated instruments in a telescoping manner over the centering rod and into the intramedullary cavity to create a canal suitable for receiving a bone prosthesis. The cannulated instrumentation includes a cannulated tamp, a cannulated osteotomy guide, a cannulated reamer, a cannulated box chisel, and a cannulated broach. The instrumentation is also disclosed.

8 Claims, 7 Drawing Sheets

CANNULATED TAMP AND CENTERING ROD FOR TOTAL JOINT ARTHROPLASTY

CROSS REFERENCES TO RELATED CO-PENDING APPLICATIONS

This application is a continuation-in-part application of: co-pending U.S. patent application Ser. No. 08/528,063, filed Sep. 14, 1995, titled CANNULATED BROACH FOR TOTAL JOINT ARTHROPLASTY now U.S. Pat. No. 5,601,564 issued Feb. 11, 1997, which is a continuation of U.S. patent application Ser. No. 08/158,603, filed Nov. 24, 1993, titled CANNULATED INSTRUMENTATION FOR TOTAL JOINT ARTHROPLASTY AND METHOD, now abandoned; and is related to co-pending U.S. patent application Ser. No. 08/728,300, filed concurrently with this application and titled CANNULATED INSTRUMENTATION FOR TOTAL JOINT ARTHROPLASTY AND METHOD.

FIELD OF THE INVENTION

The present invention relates to an apparatus and method of preparing a bone for total joint arthroplasty, and more specifically to instrumentation used in the method of preparation of the cortical and intramedullary cancellous bone to receive a joint prosthesis.

BACKGROUND OF THE INVENTION

In the elderly and severely injured, total joint arthroplasty or replacement is often required in order for a patient to have any chance of returning to normal function and ambulation. Orthopaedic surgeons have successfully implanted total joint systems into patients for many years. Although these systems have proven successful over long periods, surgeons are constantly attempting to increase the success rate of total joint arthroplasty.

Total joint replacement requires an involved surgical procedure conducted by a trained surgeon. To accomplish a total joint replacement, a surgeon first gains access to the damaged joint through an incision in the overlying skin, muscle and connective tissue including the joint capsule. Then the damaged joint, which includes the articular surface as well as the subtending cortical and intramedullary cancellous bone, is removed. A cavity is then created within the intramedullary cancellous bone in the shape of the prosthetic anchoring stem. The prosthetic joint is sized and then the anchoring stem is placed within the cavity. The prosthesis may or may not be cemented which is dependent on the type of stem used on the prosthesis. Finally, the surgical wound is then closed.

Using the femur as a more specific example, the femur has several regions that are generally common to all long bones. There are articular joint surfaces at both ends separated by a "hollow" shaft. The outer layer of the bone, the so-called "shaft" portion, is comprised of a hard dense cortical bone layer which is thin at the ends of the bone and fairly thick through the middle portion of the shaft. The inner portion of the bone that the cortical bone layer surrounds is the marrow portion of the bone known as the intramedullary cavity which is somewhat misnamed because it is not empty as the word "cavity" would imply, but rather is comprised of cancellous bone which has a lattice like structure. The spaces between the lattices is usually filled with either fat cells or blood producing cells. Cancellous bone is significantly weaker when compared to cortical bone, but contributes substantially to force dispersion through the lattice network.

The femur also has several regions beginning with a proximal head which is the round articular joint portion involved in the hip joint. The head is supported by the femoral neck which projects out of the femoral shaft at an angle to the shaft proximate the greater and lesser trochanteric regions of the femur which are areas of major muscular attachment to the femur. The femoral shaft ends distally at the two femoral condyles which carry the articular surfaces that, with the proximal tibia, form the knee joint. The proximal femoral cortical bone is thinnest about the femoral head and trochanteric regions and gradually thickens towards the middle of the shaft. The shaft is also at its smallest diameter at midshaft and thus the intramedullary cavity "funnels" down to the mid shaft. It is within this "funnel" that the surgeon wishes to implant the stem of the femoral component for the total hip prosthesis. In order to accomplish this, the surgeon must gain access to the intramedullary cavity and shape the cancellous bone into the desired shape to receive the anchoring stem of the prosthesis.

After exposing the proximal femur and hip joint, the proximal end of the femoral neck is osteotomized. To accomplish this, a gauge or osteotomy template is placed proximate the femur to provide the surgeon with a reference to decide where to sever the femoral neck, usually just proximate the trochanteric region. Once the femoral neck is removed, the intramedullary cavity with its cancellous bone is exposed and ready to be prepared to accept the anchoring stem of the femoral component of a total hip prosthesis. A few instruments are used in this procedure. These include a reamer, a broach, and optionally, a box chisel. All of these instruments are commonly known in the art of orthopaedic surgery.

A reamer is first positioned into the cancellous bone of the femoral intramedullary cavity. While inserting the reamer, the surgeon rotates the reamer to sever the cancellous bone and to create an intramedullary canal. When the surgeon feels that enough cancellous bone is severed, the surgeon removes the reamer from the femoral intramedullary canal.

A box chisel is next optionally employed. The box chisel is used in the cavity to prepare the femur for improved broaching and to orient the broach for proper placement and anteversion. The box chisel prepares the opening of the cavity to comply with the cross-sectional geometry of a broach which is substantially rectangular in shape. A mallet or hammer is used to chisel the cancellous bone until the box chisel reaches the appropriate depth. The box chisel is then removed.

A broaching instrument, or simply called a broach, is next inserted into the intramedullary canal to create a canal geometry compatible with the prosthesis geometry. The surgeon must take care to insert the length of the broach along the same axis formed by the reamer. The surgeon impacts the protruding surface of the broach with a mallet or slide hammer until the collar of the broach is properly seated on the severed femoral neck surface.

A provisional neck is next placed in the broach to ascertain proper neck length of the prosthesis. The provisional neck is adjusted until proper reduction is achieved to allow for proper range of motion in the joint. The adjustment measurements are recorded and the provisional neck is then detached and the broach is removed from the intramedullary canal.

Finally, after the preceding preparation is complete, the femur is now ready to accept the femoral stem of a hip prosthesis that is chosen to match the measurements taken with the provisional in place. The femoral stem is cemented or press-fit into place and is now ready to accept the ball portion of the joint.

In the past, surgeons have employed a flexible wire in the above-described procedure. The wire was inserted into the length of the bone before reaming. The wire served as a guide over which a flexible reamer having a longitudinal bore therein was telescopically placed. Since the wire was flexible, it did not successfully serve as a guide for intramedullary canal preparation because the guide was not stationary. Instruments placed along or over the wire were free to move within the canal as freely as if no guide wire existed. Only flexible instrumentation was used in the prior art procedures which limited the surgeon's ability to effectively prepare the bone for accepting a prosthesis. The bores in the instruments were very small in diameter since the bores only had to fit over a wire having a diameter of up to about 1 millimeter.

When preparing a bone for a prosthesis, surgeons have consistently been met with the problem of locating the central axis of a bone along which to create the intramedullary canal and ultimately becoming the axis along which the prosthesis will align. Location of the central axis of the bone is critical for a successful operation. If the prosthesis is not centered, uneven weight distribution occurs which causes problems both with respect to the remaining bone and the prosthesis. Since the entire bone is not exposed during total arthroplasty, the surgeon has only a limited view of a portion of the bone. Therefore, locating the bone's longitudinal axis is exceedingly difficult. To date, orthopaedic surgeons have not had reliable methods of successfully or accurately locating a bone's central axis.

The above-described procedure is met with other difficulties. If the surgeon does not insert the broach into the same cavity that the reamer was placed, the surgeon may easily crack the patient's bone. This results in prolonged surgery and prolonged healing time necessitated by the repair of the crack. The surgeon must also take care not to create a canal which is exceedingly large and therefore is not suited to receive a prosthesis.

The present invention helps to alleviate the above cited problems inherent in preparing an intramedullary canal of a bone for total joint arthroplasty. The present invention provides a method of preparing the bone and instrumentation used to conduct the method.

SUMMARY OF THE INVENTION

The present invention provides a method of preparing an intramedullary canal of a bone for total joint arthroplasty. The invention further includes instrumentation necessary to conduct the disclosed method.

The method for preparing an intramedullary canal of a bone for total joint arthroplasty is disclosed. The method comprises drilling a pilot hole through a point in the cortical bone layer and into the intramedullary cavity of the bone near the articulating surface of the bone. There is a point on the cortical surface of the femur, for example, that is a notch on the cephalad surface of the femur very near the junction of the base of the neck of the femur with the greater trochanteric region. This notch is on the longitudinal axis of the shaft and the intramedullary cavity. For the femur, this notch is used to place the pilot hole. Next, a substantially rigid centering rod is inserted into the pilot hole formed by the drill and driven into the intramedullary cavity of the bone by driving the centering rod through the cancellous bone until the rod is imbedded in the cancellous bone. This causes the centering rod to align with the center axis of the bone. This is a simple, nearly fool proof method of finding the central longitudinal axis of the bone. It also provides a guide with which the surgeon can routinely prepare an intramedullary canal for receiving a prosthesis anchoring stem.

An osteotomy template including a cannulated securement device is next inserted over the centering rod. Using the template as a guide, the bone is marked for osteotomization in alignment with the longitudinal axis. The articulating surface of the bone is then osteotomized to expose the intramedullary cavity of the bone.

A substantially rigid cannulated reamer is telescopically placed over the centering rod and the cancellous bone is reamed to sever the cancellous bone and create the beginnings of an intramedullary canal. After reaming is complete, the reamer is removed from the intramedullary canal and from the centering rod. A substantially rigid cannulated broach is next telescopically placed over the centering rod and into the intramedullary canal. The centering rod provides a reproducible alignment with the central longitudinal axis of the femur upon which the cannulated orthopaedic instrumentation is placed. The centering rod ensures that the instrumentation is placed along the same axis throughout the procedure.

The centering rod is next removed and a provisional neck is placed into the broach and adjusted to achieve proper neck length for a trial reduction. Once the provisional neck is adjusted to achieve proper range of motion, the provisional neck measurements are taken and the provisional neck and broach are removed from the bone. Upon completing this procedure, preparation of the bone is complete and the bone is ready to accept the prosthesis.

An embodiment of the present invention comprises a substantially rigid centering rod inserted through a pre-drilled pilot hole and driven into the cancellous bone of the intramedullary cavity over which the femoral neck and head can be osteotomized and then over which a cannulated tamp passed. The cannulated tamp is then driven into the intramedullary cavity, crushing and compacting the native cancellous bone all the while being guided down the longitudinal axis of the femur by the centering rod. When finally seated, the cannulated tamp is able to receive provisional necks for the measuring of articulation of the reduced joint. The cannulated tamp is substantially the same shape as the anchoring stem of the prosthesis to be implanted and therefore an intramedullary canal suitable for receiving the anchoring stem of the prosthesis is created with the passage of a single instrument into the intramedullary cavity.

The present invention also provides a substantially rigid centering rod, a substantially rigid cannulated reamer, a substantially rigid cannulated broach, a cannulated box chisel, and a cannulated osteotomy template. The cannulated instruments, when used in accordance with the method of the invention provide a nearly foolproof method of preparing an intramedullary canal in a bone suitable for completing the joint arthroplasty. The present invention aids the surgeon in preparing a properly sized and placed intramedullary canal in the intramedullary cavity for successful placement and retention of a prosthesis. The present method and instrumentation offers a surgeon the ability to avoid several typical surgical complications. This helps to reduce the length of the surgery. This is particularly important with elderly patients because it is important to limit the time the patient is anesthetized. Additionally, the procedure reduces the time that an operating room is occupied thus reducing overall health care costs. The present invention also reduces the likelihood of cracking a bone while preparing its intramedullary canal for a prosthesis.

Other objects of the present invention and many of the attendant advantages of the present invention will be readily appreciated as the same become better understood by reference to the following detailed description when considered in connection with the accompanying drawings.

DETAILED DESCRIPTION OF THE INVENTION

The procedures and instrumentation used in the present invention are shown generally in FIGS. 1 through 16. For purposes of description only, a femur is discussed in this detailed description. One skilled in the art will recognize that the procedure and instrumentation of the present invention is equally useful to prepare any intramedullary cavity of any bone for receiving a prosthesis.

After making an incision proximate the joint needing arthroplasty, the surgeon temporarily displaces overlying and surrounding tissue from the articulating surfaces of the joint. For purposes of description only, if a hip arthroplasty is described, the surgeon displaces the tissue from over and around the proximal end of the femur and acetabulum. As is commonly known in the art, it is very important to align the center of the created intramedullary canal within the central longitudinal axis of the bone. If a prosthesis is not placed along the central longitudinal axis, uniform stress distribution is not achieved. After disarticulating the joint, the surgeon drills a pilot hole centered on the longitudinal axis of the femoral shaft through the cortical bone and into the intramedullary cavity of the femur near the articulating surface needing replacement. A qualified surgeon determines where to drill the entry point, or pilot hole, by reviewing preoperative x-rays. The decision over placement of the drill is a technique commonly known in the art by orthopaedic surgeons.

Figure 1:
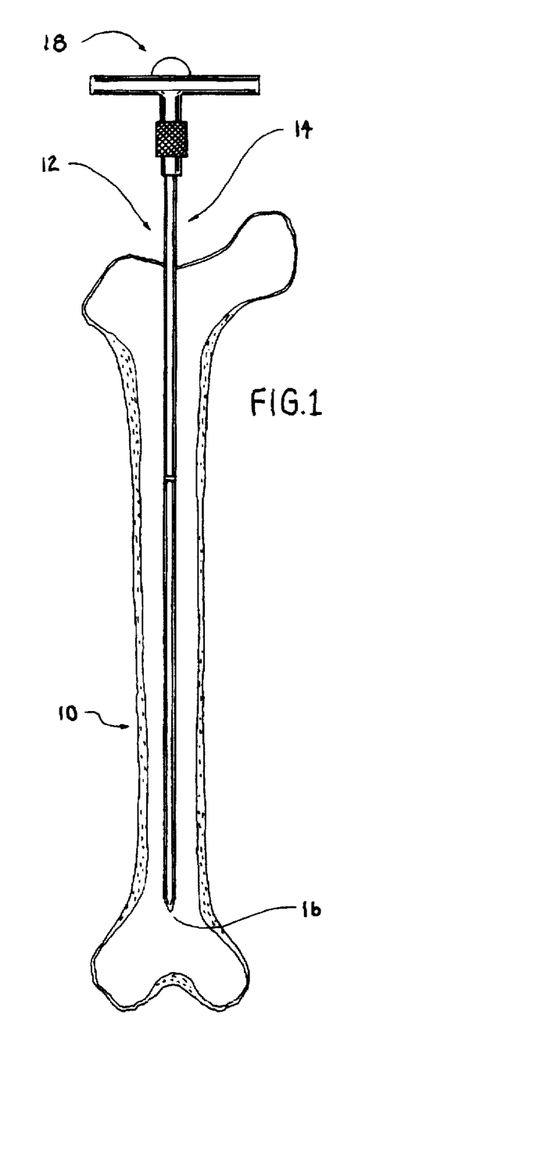
FIG. 1 is a side elevational view of an embodiment of the centering rod of the present invention and a longitudinal cross sectional view of a femur with the centering rod of the present invention inserted into the intramedullary cavity of the femur.

FIG. 1 generally shows a femur 10. A hole is drilled into the proximal portion or first end of the femur at 12. Once the surgeon has drilled into the intramedullary cavity at 12, the surgeon then drives a substantially rigid centering rod 14 longitudinally into the intramedullary cavity of the femur along the femur's longitudinal axis. Preferably, the surgeon continues to insert the centering rod until it becomes embedded within the cancellous bone.

Although centering rod 14 is preferably formed of stainless steel, any rigid material commonly used in the art of orthopaedic surgery instrumentation may be employed. The critical feature of centering rod 14 is that it is rigid for first locating the central axis of the bone and second, to act as a guide for preparation of the intramedullary canal. This is discussed more fully below.

Centering rod 14 may vary in size depending upon the overall size of the patient's bone. Centering rod 14 ranges in size from about 3 to about 9 millimeters in diameter by about 100 to about 600 millimeters in length. Preferably, the centering rod of the present invention is about 6 millimeters in diameter and about 450 millimeters in length. A centering rod tip 16 is preferably pointed to facilitate driving and placement of centering rod 14 into the intramedullary cavity. Rod tip 16 comprises about 5 degrees to about 45 degrees of bevel and preferably about 24 degrees.

As shown in FIG. 1, a handle 18 may be placed at the free end of centering rod 14. Handle 18 provides a means for the surgeon to insert or, if needed, to impact the rod with a mallet, or remove the rod. Once centering rod 14 is placed, the bone is ready for osteotomization or cutting to expose the intramedullary cavity for preparation of the canal.

Figure 2:
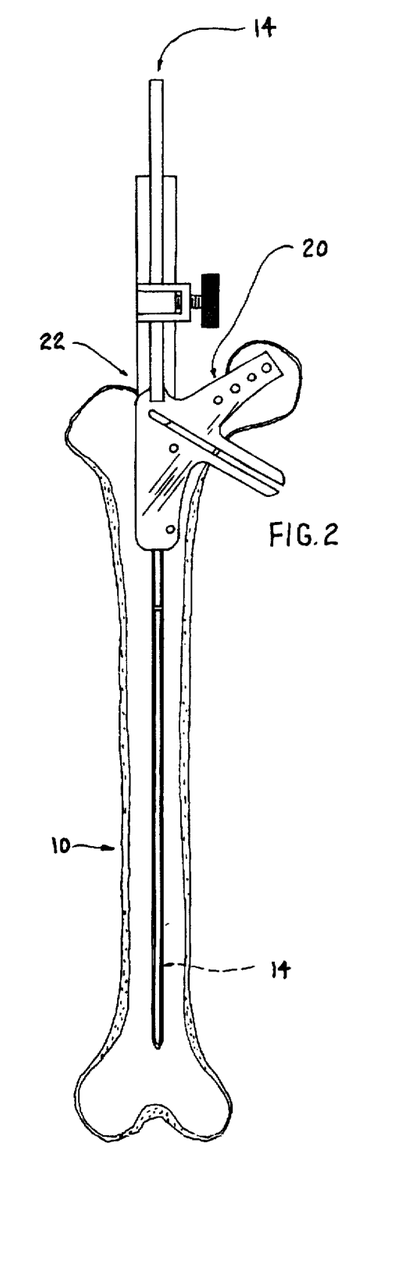
FIG. 2 is a side elevational view of the centering rod of FIG. 1 and further including an osteotomy guide having a cannulated securement device telescopically placed over the centering rod.
Figure 7:
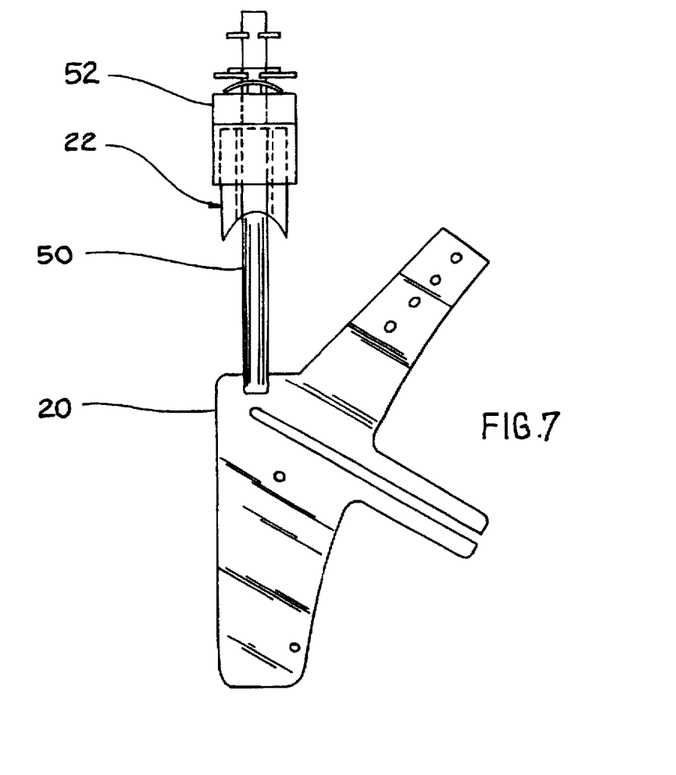
FIG. 7 is a side elevational view of the osteotomy guide depicted in FIG. 2.
Figure 8:
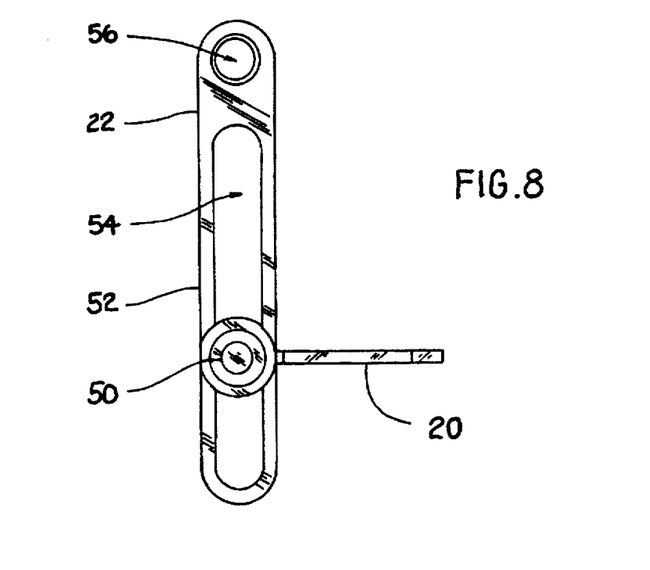
FIG. 8 is a top plan view of the osteotomy guide shown in FIG. 7.

The present invention utilizes an osteotomy guide 20 or template, as shown in FIGS. 2, 7 and 8, which includes a rotatable cannulated securement guide 22. The surgeon places a cannulated bore 56 of securement means 22 over centering rod 14. Centering rod 14 provides a means of accurately orienting the osteotomy cut to the longitudinal axis of the bone. This direct orientation of osteotomy guide 20 to the bone's longitudinal axis is a great advancement in orthopaedic surgery. As is commonly known, most bones are not flat and an osteotomy template does not generally rest upon a bone surface without moving or slipping making it difficult to orient the template. A cannulated securement device 22 attached to osteotomy guide 20 provides assurance to the surgeon that the osteotomy guide 20 does not move even while first scoring and then cutting the bone until removed by the surgeon.

Generally, the securement guide 22 comprises a rod 50 which extends vertically from osteotomy guide 20. A sliding actuating guide 52 is placed over rod 50. Sliding guide 52 contains two apertures therein. The first aperture is an elongated opening 54 which receives rod 50. Rod 50 is allowed to slide inside the length of elongate opening 54. The second aperture in sliding actuating guide 52 is a bore 56 which is suited for telescopically receiving centering rod 14. When bore 56 is placed over centering rod 14, osteotomy guide 20 is centered along the longitudinal axis of bone 10. Securement guide 22 ensures that the osteotomy cut is accurately oriented to the long axis of bone 10 since only a small portion of the bone is visible during the operating procedure. Osteotomy guide 20 and rotatable cannulated securement guide 22 is preferably manufactured from stainless steel, although any material commonly known in the art of orthopaedic instruments may be used to form the device.

Figure 3:
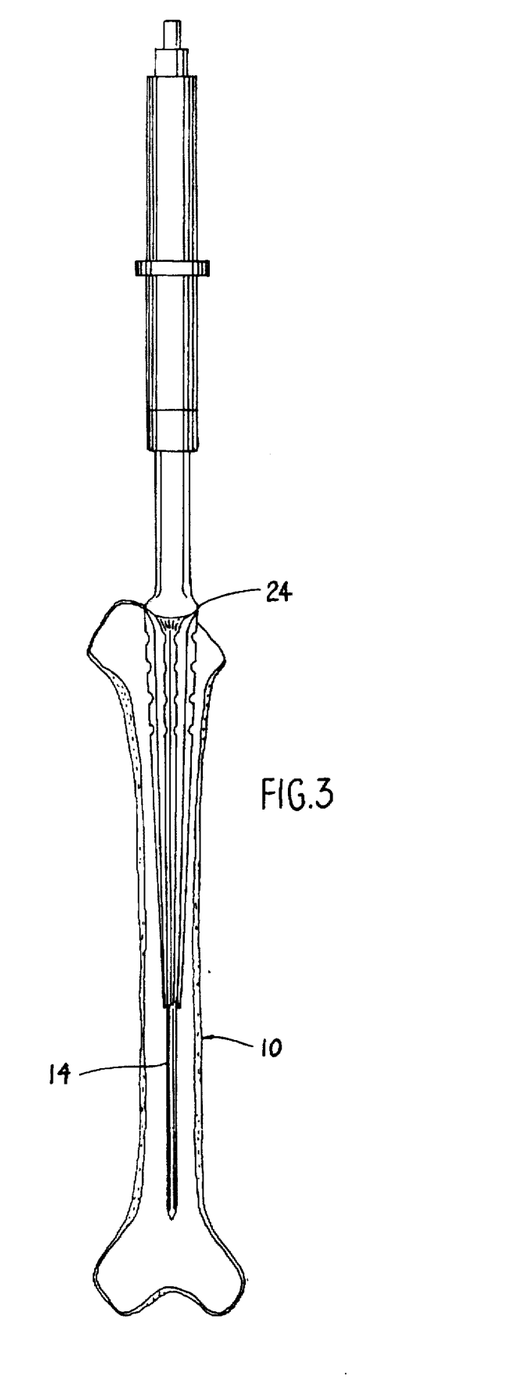
FIG. 3 is a side elevational view of a reamer embodiment of the present invention placed over the centering rod of FIG. 1 and into the intramedullary cavity of the femur.

The intramedullary cavity is now exposed and the surgeon proceeds to the steps of preparing the cavity for receiving an anchoring stem of a prosthesis. The surgeon next telescopically places a substantially rigid cannulated reamer 24 over centering rod 14, as shown in FIG. 3. The surgeon then advances and rotates reamer 24 along centering rod 14 and into the intramedullary cavity of bone 10. Cancellous bone is severed from the intramedullary cavity when the surgeon rotates reamer 24. Once a surgeon determines enough tissue is severed, the surgeon removes cannulated reamer 24 from the bone and centering rod 14.

Figure 9:
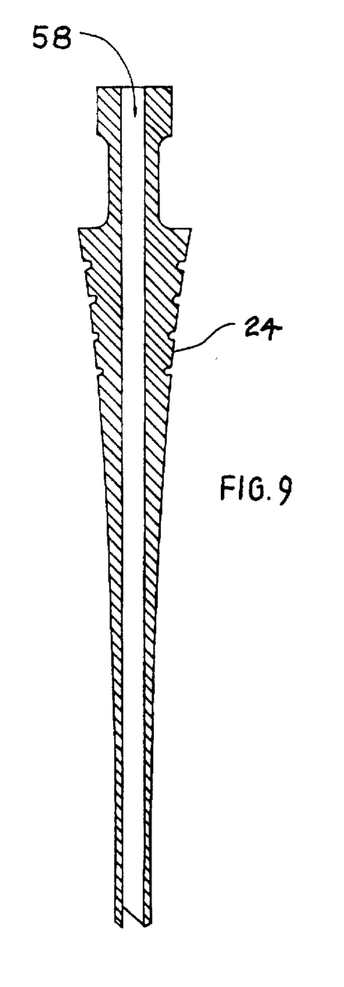
FIG. 9 is a longitudinal cross-sectional view of the reamer depicted in FIG. 3.

Reamer 24 of the present invention is similar to those reamers commonly known in the art of orthopaedic surgery having longitudinal flutes extending the length of the tissue-contacting portion of the reamer. As shown in FIG. 9, reamer 24 of the invention further includes a longitudinal bore 58 which centrally traverses the length of reamer 24. Bore 58 extends the length of reamer 24 to provide reamer 24 to telescopically receive centering rod 14. Although a tapered reamer is shown in the Figures, any type of reamer cutting surface may be adapted to a cannulated reamer according to the present invention. If, however, reamer 24 contained an excessively long handle portion, bore 58 would not necessarily be required to pierce the length of the handle to allow reamer 24 to function appropriately in the method of the present invention. This is the case for each cannulated instrument described herein. Reamer 24 of the present invention is formed of substantially rigid material such as stainless steel, titanium, cobalt and chrome, or composites thereof Preferably, stainless steel is used.

A direct result and advantage to the method of utilizing centering rod 14, is that a reamer such as reamer 24 may have a larger diameter and more aggressive fluting 60 thereon can be utilized to sever the tissue from the intramedullary cavity. Therefore, a larger canal is created in the intramedullary cavity of the bone 10 for increased success of placing a broach.

By using centering rod 14, a surgeon is able to control preparation of the intramedullary cavity. For example, the surgeon does not have to worry that the reaming action will not extend along the longitudinal axis of the bone. Therefore, there is less concern with respect to whether or not an excessively large cavity is created which is not suitable for receiving and maintaining a prosthesis. Likewise, less concern exists regarding cracking the bone. A surgeon is less likely to jar the reamer outside of the cavity and crack the cortical portions of the bone.

Figure 4:
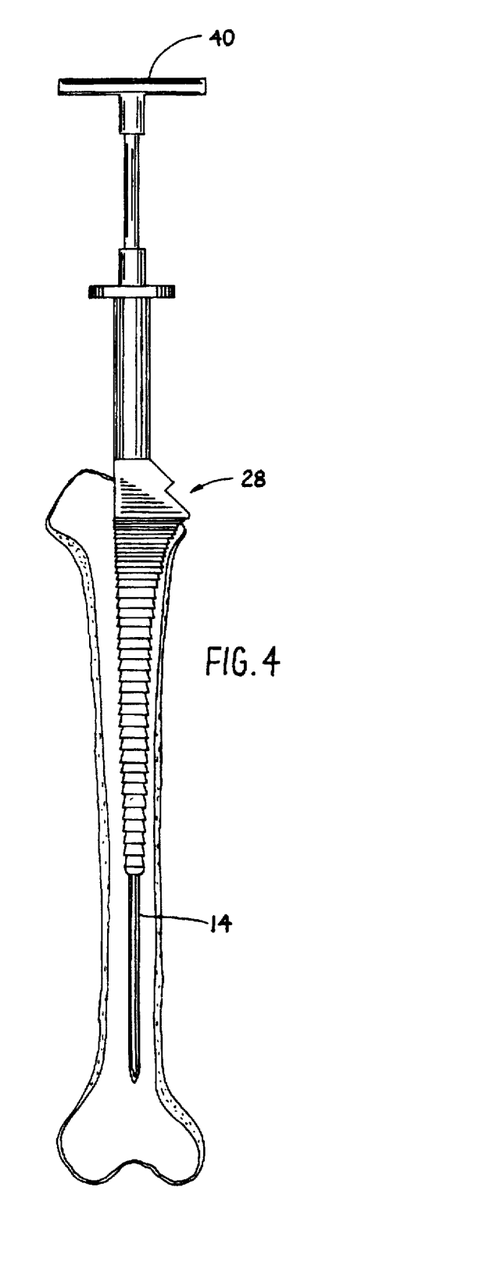
FIG. 4 is a side elevational view of a broach embodiment of the present invention telescopically placed over the centering rod of FIG. 1 and into the intramedullary cavity of the femur.

After an appropriate amount of tissue is severed, the canal is next ready for broaching. Again, the method of the present invention utilizes a cannulated instrument. A surgeon telescopically places a broach 28 having a central longitudinal bore 62 over centering rod 14, as shown in FIG. 4. As described with reamer 24, longitudinal bore 62 extends through the length of broach 28. Longitudinal bore 62 provides for broach 28 to telescopically receive centering rod 14. By placing the broach over centering rod 14 and into the intramedullary cavity of the bone, a surgeon is assured of consistently employing the broach along the longitudinal axis of the bone as represented and held in place by centering rod 14 and therefore inserting broach 28 into the exact same canal as previously created by reamer 24. Again, there is less likelihood of cracking the cortical portion of the bone using the instrumentation and method of the present invention.

The broaching surface of broach 28 of the present invention may be similar to those known in the art, however, as discussed, the broach of the present invention includes a longitudinal bore 62. Broach 28 is further formed of any material commonly known in the art of orthopaedic instrumentation, including but not limited to stainless steel, cobalt chrome, titanium, or composites thereof Preferably, stainless steel is used to make broach 28 of the invention.

Figure 5:
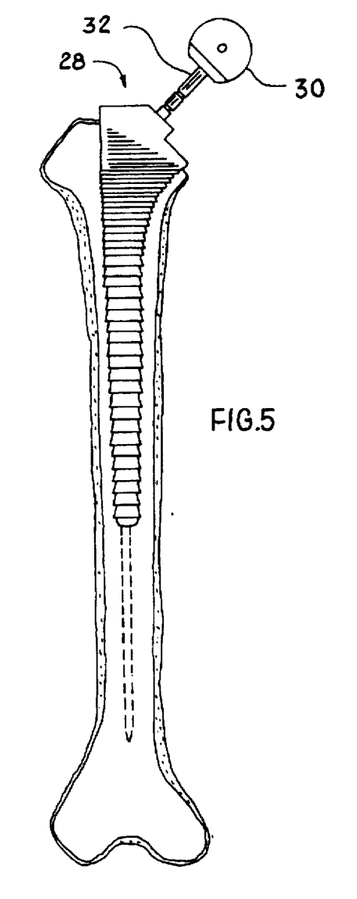
FIG. 5 is a side elevational view of the broach embodiment of FIG. 4 wherein the centering rod has been removed and a provisional neck is placed on the broach.
Figure 6:
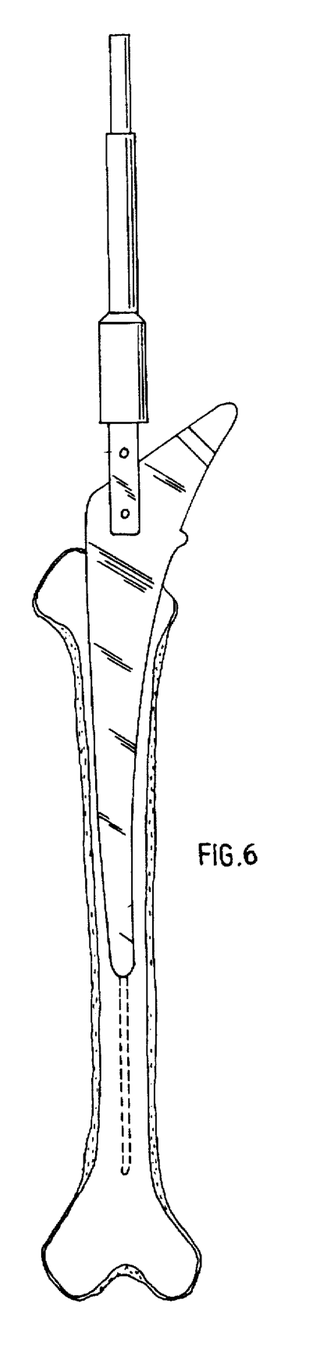
FIG. 6 is a side elevational view of a femoral portion of a total hip prosthesis in the intramedullary canal of the femur.
Figure 10:
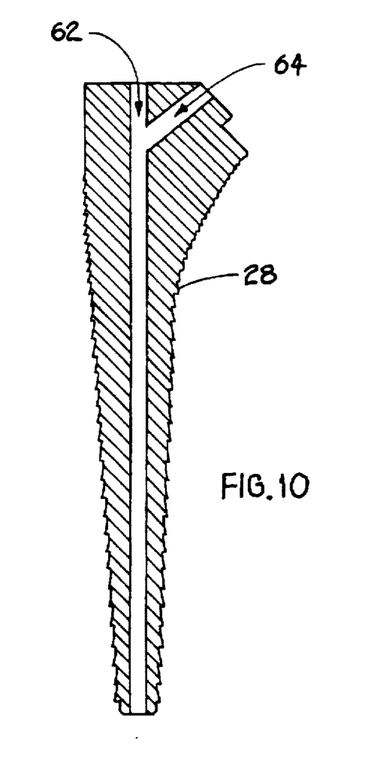
FIG. 10 is a longitudinal cross-sectional view of the broach depicted in FIG. 4.
Figure 11:
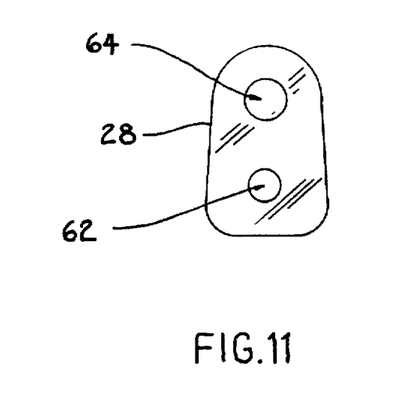
FIG. 11 is a top plan view of the broach depicted in FIG. 4.

Once broach 28 is securely in place, centering rod 14 may be removed from both the bone and broach 28. A provisional neck 30 is then placed into a diagonal bore 64 of broach 28, as shown in FIGS. 5 and 10. Diagonal bore 64 accepts a stem 32 of provisional neck 30 providing the surgeon the ability to determine proper neck length by performing a trial reduction. The length of provisional neck 30 is adjusted to achieve proper range of motion at the hip. Broach 28 and provisional neck 30 are now removed from bone 10. The cavity is now prepared with a canal and ready to receive a prosthesis.

Any type of prosthesis may be employed in the present invention including but not limited to a cemented or a press-fit prosthesis.

Figure 12:
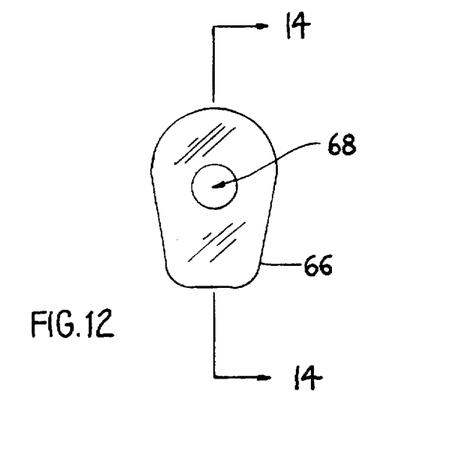
FIG. 12 is a top plan view of a box chisel embodiment of the present invention.
Figure 13:
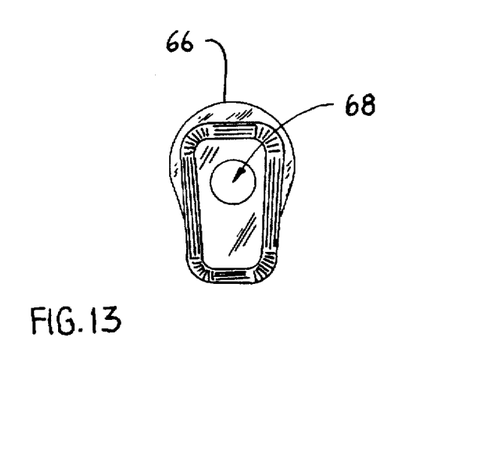
FIG. 13 is a bottom plan view of the box chisel depicted in FIG. 12.
Figure 14:
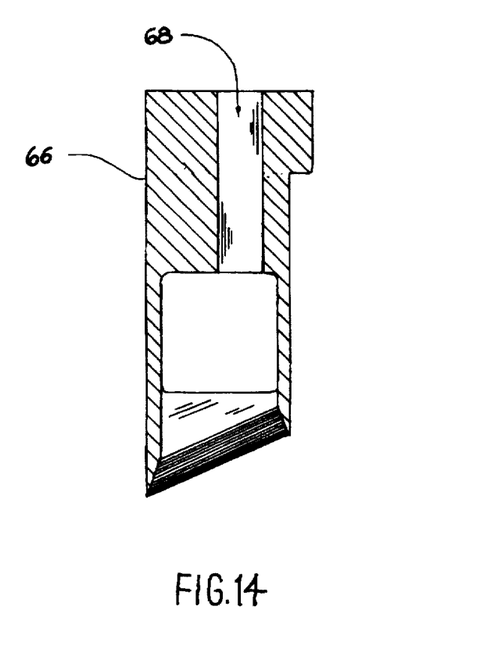
FIG. 14 is a cross-sectional view of the box chisel depicted in FIG. 12 taken along line 14—14 of FIG. 12.
Figure 15:
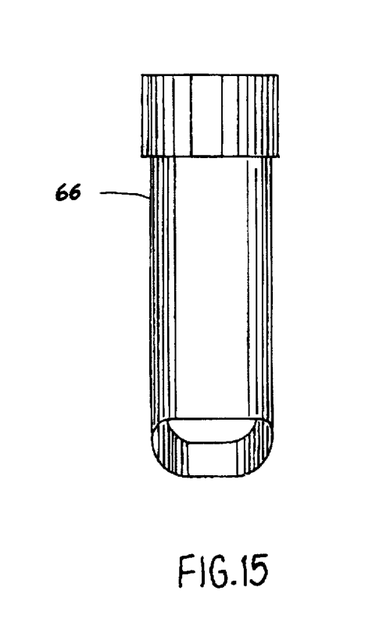
FIG. 15 is a rear side elevational view of the box chisel depicted in FIG. 12.

Optionally, the method of the present invention may include an intermediate step using a cannulated box chisel 66. Box chisel 66, as shown in FIGS. 12 through 14 is cannulated to telescopically receive centering rod 14. Box chisel 66 is inserted over centering rod 14 and into the intramedullary cavity after the reaming step is complete and before a broach is to be used. Box chisel 66 includes a longitudinal bore 68 which extends through box chisel 66. Box chisel 66 creates a canal having compatible geometry with that of the prosthesis chosen by the surgeon for use in the patient. That is, box chisel 66 creates a canal at the proximal end of the femur useful for those prostheses having this geometry as a portion of the anchoring stem. Again, the method and instrumentation of the present invention allows the surgeon to chisel the bone without an undue concern for breaking or cracking the cortical portion of the bone. The surgeon is further assured that the chiseled area is in the correct alignment along the central longitudinal axis of the bone.

Figure 16:
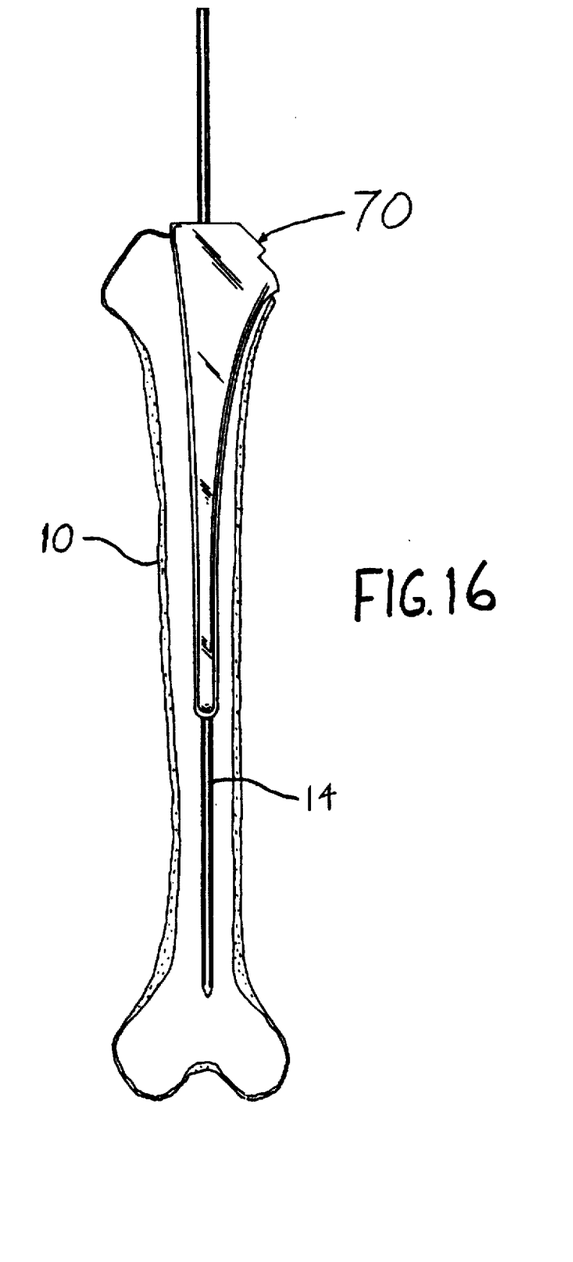
FIG. 16 is a side elevational view of a cannulated tamp embodiment of the present invention inserted over a centering rod embedded within a patient's femur shown with the femoral head and neck osteotomized.

A preferred embodiment to the present invention method and instrumentation is depicted in FIG. 16 as a cannulated tamp 70 for placement over centering rod 14 embedded in femur 10 as the immediate step after osteotomization of the femoral head and neck. Just as broach 28, as shown in FIG. 5, is able to receive provisional neck 32 carrying provisional head 30, so also may tamp 70 be equipped to receive a provisional head and neck. Tamp 70 of the present invention is formed of substantially rigid material such as stainless steel, titanium, cobalt and chrome, or composites thereof. Preferably, stainless steel is used.

In this preferred embodiment, after embedding centering rod 14 and completing the osteotomization of the native femoral head and neck, instead of proceeding with the steps described hereinabove, tamp 70 is placed over centering rod 14 in slidable telescopic engagement and then driven directly into the intramedullary cavity along the central longitudinal axis of the femur as defined by the placement of centering rod 14. As tamp 70 is driven into the intramedullary cavity, tamp 70 crushes the lattice like structure of the native cancellous bone and compacts the native cancellous bone forming a canal within the intramedullary cavity that has the same shape as the outer surface of tamp 70.

The development of a tamp such as tamp 70, provides the surgeon the choice of using a tamp that has the same geometry as the anchoring stem of the prosthesis chosen by the surgeon for the patient to receive. Centering rod 14 may be removed with tamp 70 remaining in place. With tamp 70 in place and using a provisional head and neck placed in a diagonal side bore of tamp 70, along with trial reductions, the size for the prosthesis may be determined, just as was done following the broaching step hereinabove. Consequently, the steps of reaming and broaching along with the optional step of chiseling are not necessary when using tamp 70 in conjunction with centering rod 14.

The long term complications of an implanted prosthesis includes mechanical failure of the implantation of the anchoring stem. One of the more common is failure secondary to micromotion of cemented femoral components under load. In a laboratory study on cadaveric femurs measuring the effect of a load in six translational and rotational directions, femoral component stability was evaluated for this preferred method of the present invention. A prior art method of implantation was compared to the preferred method of the present invention disclosed hereinabove using cannulated tamp 70 as a one step method and instrument to create a suitable intramedullary canal for receiving an anchoring stem of a prosthesis.

In the experiment, each femur and cemented femoral component was subjected to two types of external loads representing the stance phase of level walking and stair climbing and three dimensional micromotion was measured. The mean magnitudes of the vectors of the x, y, and z translations for the proximal position of the motion measuring device for the combined loading conditions were 8.1 microns for the compaction method of the present invention and 45.3 microns for the prior art method. For the distal position of the motion device, the mean magnitudes of the translation vectors were 8.8 microns for the compaction method of the present invention and 27.5 microns for the prior art method. The preferred method and instrumentation of the present invention has lead to an unforeseen and substantial improvement in the stability of the implanted femoral component in total hip arthroplasty.

The longitudinal bores in the instrumentation are of a suitable diameter to telescopically receive and advance along a centering rod. The instrumentation bores are preferably of uniform diameter in a particular instrument but may vary in size depending upon the diameter of the centering rod utilized in a particular procedure. The longitudinal bores of the instrumentation are greater than about 3 millimeters in diameter and preferably about 6 to about 8 millimeters in diameter. The size of the longitudinal bore is directly correlated to the size of the centering rod utilized which is dictated by the size of the bone being prepared for a prosthesis.

The overall size of the instrumentation of the present invention is also variable. As is commonly known in the art, the size of instruments used during a particular procedure depends upon the size of the bone being prepared for a prosthesis. The present invention anticipates this size variability. Therefore, one can manufacture the cannulated instruments of the present invention in any size suitable for orthopaedic surgery.

In addition to helping the surgeon reduce the chances of cracking the cortical portion of the bone and allowing a surgeon a greater opportunity to place a prosthesis along the central longitudinal axis of a bone, the present method and instrumentation has other advantages over the prior art. The present invention facilitates a more routine surgical procedure. A surgeon is afforded a greater likelihood of successful surgery if the operation proceeds in a routine manner. A routine surgery also reduces time spent conducting the surgery. This reduces both the amount of time that a patient is under general anesthesia and also reduces the amount of time the operating room is occupied. Operating rooms are exceedingly expensive in today's marketplace and the present invention helps to reduce these health care costs.

The present invention also reduces the likelihood that an excessively large cavity is prepared for the prosthesis. Also, because the prosthesis is more likely to be placed along the central longitudinal axis of the bone, the patient has more uniform stress distribution when placing his or her weight on the prosthesis. Additionally, routine surgery leads to quicker healing time and allows a patient to ambulate more quickly after surgery.

One skilled in the art will recognize that the details of the previous embodiment may be varied without departing from the spirit and scope of the invention.

We claim:

1. A method of preparing a bone for artificial joint replacement using a joint prosthesis, the bone having a longitudinal axis, at least one joint surface, an outer cortical bone surface and layer defining an intramedullary cavity, and an inner cancellous bone within the intramedullary cavity, the method comprising the steps of:

drilling a pilot hole through a predetermined point on the bone's cortical bone surface into the intramedullary cavity to the inner cancellous bone;

providing a centering rod sufficiently rigid as to be capable of being driven through the inner cancellous bone;

inserting the centering rod longitudinally into said pilot hole;

driving the centering rod through the inner cancellous bone within the intramedullary cavity in alignment with the longitudinal axis of the bone;

osteotomizing the joint surface;

providing a cannulated tamp for shaping the inner cancellous bone having a longitudinal bore extending through its length for receiving the centering rod in slidable telescoping engagement therein; and driving the cannulated tamp along the centering rod into the inner cancerous bone creating a cavity in the inner cancellous bone suitable for receiving the joint prosthesis.

2. The method of claim 1 wherein the bone prepared for artificial joint replacement is a femur.

3. An orthopedic surgical instrument apparatus for use during an arthroplasty on a bone of a patient, the bone having a joint surface, a native cortical bone outer layer defining an intramedullary cavity, and a native cancellous bone within the intramedullary cavity, the apparatus comprising:

a cannulated tamp, adapted for tamping the native cancellous bone of a patient, having a longitudinal bore extending through the length of the cannulated tamp; and a centering rod, having a smooth surface and a uniform diameter ending in a tapering distal tip, the centering rod sufficiently rigid to be driven through the native cancellous bone of a patient and become substantially embedded within the native cancellous bone, the centering rod having an outer diameter substantially equivalent to an inner diameter of the longitudinal bore so as to be telescopically slideably engageable within the longitudinal bore, wherein the centering rod is positionable in the longitudinal bore for guiding the cannulated tamp along the centering rod's longitudinal axis.

4. The apparatus of claim 3 in which the longitudinal bore has a diameter of between about 3 and about 9 millimeters.

5. The apparatus of claim 3 in which the cannulated tamp and centering rod include constructing with at least one of the materials selected from a group consisting of stainless steel, cobalt-chrome alloy and titanium.

6. The apparatus of claim 3 in which the longitudinal bore has a diameter of about 6 millimeters.

7. The apparatus of claim 3 in which the centering rod comprises a rigid shaft having a substantially uniform diameter and terminating in a tapered end.

8. The apparatus of claim 3 in which the cannulated tamp has a proximal end and a distal end with the longitudinal bore extending from the proximal end to the distal end, and further comprising a second bore extending from the proximal end diagonally intersecting the longitudinal bore.

* * * * *

UNITED STATES PATENT AND TRADEMARK OFFICE
CERTIFICATE OF CORRECTION

PATENT NO.  : 5,800,437
DATED       : September 1, 1998
INVENTOR(S) : Gustilo et al.

It is certified that error appears in the above-indentified patent and that said Letters Patent is hereby corrected as shown below:

Col. 7, Line 47 after the word "thereof" insert --.--.

Col. 8, Line 21 after the word "thereof" insert --.--.

Col. 10, Line 57 cancel the word "cancerous" and insert the word "cancellous"

Col. 12, Line 4 after the word alloy insert --,--.

Signed and Sealed this

Twenty-fourth Day of November,1998

Attest:

BRUCE LEHMAN

Attesting Officer

Commissioner of Patents and Trademarks